(12) United States Patent
Wagner

(10) Patent No.: US 9,410,978 B1
(45) Date of Patent: Aug. 9, 2016

(54) LIQUID SAMPLE LOADER FOR ANALYTICAL INSTRUMENTS AND METHOD OF LOADING SAME

(71) Applicant: Rudolph Research Analytical Corporation, Hackettstown, NJ (US)

(72) Inventor: Jeff Wagner, Long Valley, NJ (US)

( * ) Notice: Subject to any disclaimer, the term of this patent is extended or adjusted under 35 U.S.C. 154(b) by 0 days.

(21) Appl. No.: 14/935,070

(22) Filed: Nov. 6, 2015

(51) Int. Cl.
*G01N 1/00* (2006.01)
*G01N 35/10* (2006.01)

(52) U.S. Cl.
CPC .................. *G01N 35/1097* (2013.01)

(58) Field of Classification Search
CPC ............ G01N 1/02; G01N 1/10; G01N 1/14; G01N 2001/002; G01N 2001/1445; G01N 2001/1454; G01N 35/00; G01N 35/10; G01N 35/1095; G01N 35/1097
See application file for complete search history.

(56) References Cited

U.S. PATENT DOCUMENTS

| | | | | |
|---|---|---|---|---|
| 4,014,652 A | * | 3/1977 | Ishibashi | G01N 35/08 356/36 |
| 4,023,709 A | * | 5/1977 | Becker | G01N 35/1097 222/318 |
| 4,106,671 A | * | 8/1978 | Sharples | G01N 1/38 137/386 |
| 4,827,746 A | * | 5/1989 | Kawaguchi | G01N 9/002 73/32 A |
| 6,371,331 B1 | * | 4/2002 | Gohde | B01L 3/0265 222/130 |
| 8,596,340 B1 | * | 12/2013 | Horn, Jr. | B01L 7/00 165/104.11 |
| 2011/0211189 A1 | * | 9/2011 | Ryan | A61B 3/101 356/73 |

FOREIGN PATENT DOCUMENTS

EP 0483043 A2 4/1992

* cited by examiner

*Primary Examiner* — Peter Macchiarolo
*Assistant Examiner* — Natalie Huls
(74) *Attorney, Agent, or Firm* — Kaplan Breyer Schwarz & Ottesen, LLP

(57) ABSTRACT

A liquid sample loader for an analytical instrument includes a sample holder with a sample well for holding a liquid sample and a sample passageway extending upwardly at an inclined angle from a bottom portion of the well, a pump positioned upstream from the sample holder and an upstream passageway coupled between the sample and the pump. A controller controls the pump to push the sample in the sample well downstream through the sample passageway toward the measuring instrument.

13 Claims, 3 Drawing Sheets

LIQUID SAMPLE LOADER FOR ANALYTICAL INSTRUMENTS AND METHOD OF LOADING SAME

TECHNICAL FIELD

This invention relates to analytical instruments, and in particular, liquid sample loaders for use with the analytical instruments.

BACKGROUND OF THE INVENTION

Liquid sample loaders are used to load samples into an analytical instrument for measuring various properties of the sample. Examples of analytical instruments are polarimeters for measuring the optical rotation of samples and refractometers for measuring the refractive index of samples.

Often, a laboratory worker loads the analytical instrument manually by injecting the liquid sample into the input port of the instrument with a syringe while watching for excess sample to appear at the output port to verify that the instrument is fully loaded. A tube connected to the output port carries any excess sample to a waste jar.

Once measurements are made by the analytical instrument, the liquid sample is removed. First, the syringe is removed from the input port. Then, one end of a flexible hose with the other end connected to an air pump is attached to the input port. The pump is turned on and the pump's air pressure pushes the sample in the analytical instrument out through the output port and on to the waste jar. To clean the instrument, solvents are injected and removed in a similar manner. Often the final step is to dry any residual solvent by leaving the air hose attached and the pump running for a few minutes.

One disadvantage of the above manual method is the need for a trained operator to load and handle syringes. Also, these syringes are cleaned or treated as a disposable consumable which adds a significant cost to the operation.

At the other end of the spectrum, fully automated liquid sample loaders can be used. In those devices, liquid samples are placed in vials or test tubes in motor driven racks. A robotic needle enters the liquid sample and draws it into the analytical instrument by suction. A light gate/sensor, which is an optical method of detecting the presence of the liquid sample in a transparent tube, is placed near the exit port of the analytical instrument to detect when the loading is complete. Keeping the light gate as close to the exit port as possible minimizes the volume of liquid sample required for each analysis. Cleaning solvents stored in tanks, a system of valves, and an air pump are used to clean and dry the instrument.

While the fully automated loaders offer the convenience of unattended operation, there are many disadvantages such as high cost, high maintenance, and larger size of the equipment, as well as the need to load and clean or dispose of the vials.

In between the above two types of loaders, there are semi-automated loaders for loading samples into the analytical instruments. One such loader is disclosed in U.S. Pat. No. 4,827,746 issued to Kawaguchi, which is incorporated herein by reference and is shown in FIG. 1.

A U-shaped thin oscillating tube 1, which is a part of the analytical instrument is supported by a supporter P. A magnet 2 is attached to tube 1 at the bottom of the U-shape, and oscillates together with the tube. A detection signal, which is an electric signal indicative of the oscillation of magnet 2, is generated by a detection head 3. The density of the liquid which fills tube 1 is calculated on the basis of the detection signal by a detection circuit (not shown). The detection signal is also utilized to drive oscillating tube 1 by driving head 4. One end of tube 1 is open via a sampling tube 5 in a vessel 6 in which the liquid is supplied. The liquid is introduced into tube 1 by a pump 9, which is connected to the other end of tube 1 through a valve 7 and another vessel 8.

In particular, the bottom end of sampling tube 5 draws a liquid sample from vessel 6 by suction from the pump 9. The solenoid valve 7 is closed when the loading is complete to prevent the sample from syphoning back into the vessel 6 during analysis.

While the sample loader of the above type is relatively easy to use and has a moderate cost, there are many disadvantages. First, because the sample is drawn by suction, it may not be able to handle high viscosity samples due to higher forces required or samples with components which may separate and evaporate under suction. While the 746 patent does suggest that the above method could be modified by using pressure, there is no discussion of how this can be achieved. Second, disposal or cleaning of the sampling vessel 6 needs to be done manually by removing the vessel. Third, disposal or cleaning of the outside of the sampling tube 5 needs to be done manually. Fourth, because the solenoid valve 7 is in the sample path, it is exposed to various types of samples or rinse solvents. Valves that are inert to every sample or rinse solvent that might be used can be very expensive. Moreover, valves are subject to damage from particulates and residual material that is allowed to dry within the valve. Fifth, some wasted sample is always left in the bottom of the sampling vessel 5.

Therefore, it would be desirable to provide an improved sample loader and method that overcome the disadvantages discussed above.

SUMMARY OF THE DISCLOSURE

A liquid sample loader for an analytical instrument according to one aspect of the present invention includes a sample holder with a sample well for holding a liquid sample and a sample passageway extending upwardly at an inclined angle from a bottom portion of the well, a pump positioned upstream from the sample holder and an upstream passageway coupled between the sample and the pump. The pump pushes the sample in the sample well downstream through the sample passageway toward the measuring instrument.

According to another aspect of the present invention, a method of loading a liquid sample into an analytical instrument is provided. An operator inserts a liquid sample into a sample well of a sample holder having a sample passageway that extend upwardly at an inclined angle from a bottom portion of the sample well. Then, an air pump positioned upstream from the sample holder is turned on to pump air through an upstream passageway into the sample well so as to push the sample through the sample passageway toward the analytical instrument. When the sample has been loaded into the analytical instrument, the air pump is turned off.

Advantageously, both the well and the inclined sample passageway fill from the bottom under the action of gravity, which displaces air upwards. The upward displacement of air tends to eliminate the formation of slugs of liquid sample separated by trapped air. As a result, the liquid sample travels as a single body. This allows a sample sensor located by the analytical instrument to be a reliable indicator that the sample has been loaded fully without trapped air. Also, because the loading operation uses a pressure mode of the air pump to push the liquid sample rather than pull by vacuum, the present

DETAILED DESCRIPTION OF THE INVENTION

Figure 2:
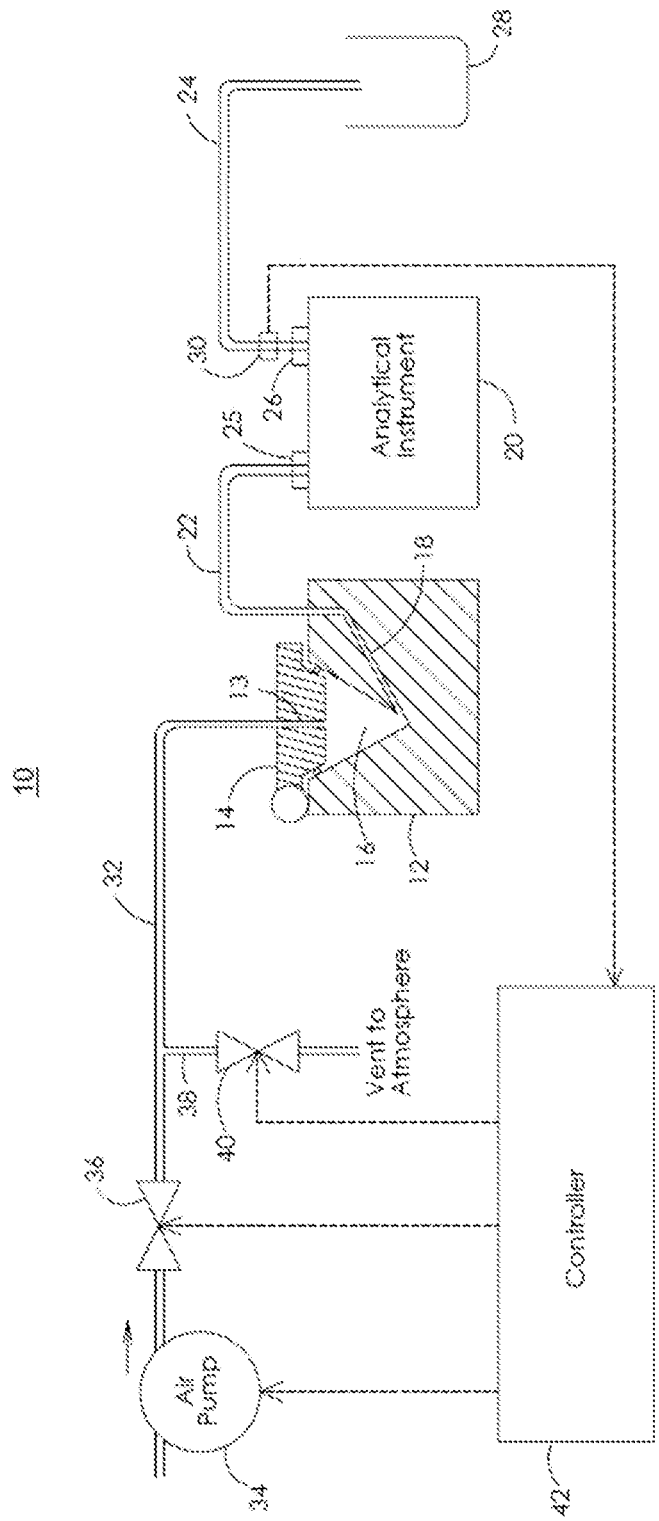
FIG. 2 illustrates an exemplary sample loader for an analytical instrument according to one aspect of the present invention.

FIG. 2 illustrates an exemplary sample loader 10 for an analytical instrument 20 according to one aspect of the present invention. A sample holder 12 includes a hinged lid 14, sample well 16 for holding the sample liquid and sample passageway/lumen 18 positioned within the holder. Once the liquid sample has been filled in the sample well 16, the hinged lid 14 fluidly seals the well 16. The sample well 16 as shown has a tapered bottom such as a conical shape and a bottom portion of the well is in fluid communication with the passageway 18 which extends from the bottom portion at a preselected upward inclined angle and has an exit point near the top of the sample well. The shape of the well 16 and the angle of the passageway 18 ensure that there are no gaps in the sample liquid to cause separate slugs of the liquid sample as it travels downstream towards an analytical instrument 20. Although the sample passageway 18 as shown in FIG. 2 extends from the tapered bottom end, it can extend from any point in the bottom portion so long as there is no gap in the sample liquid between the well 16 and the passageway to cause any separate slugs of the liquid. The angle of the inclined passageway 18 can be as high as 90 degrees from horizontal.

A transfer passageway/tube 22 connected between the top of the sample passageway 18 and an input port 25 of the analytical instrument 20 carries the liquid sample to the instrument. A waste passageway/tube 24 is disposed between an output port 26 of the instrument 20 and a waste holder/jar 28. A sample sensor 30 is located on the waste tube 24 near the output port to sense the liquid sample as it exits the analytical instrument 20. The sample sensor 30 is located near the output port 26 to reduce the waste. In one embodiment, the sample sensor 30 is an optical sensor (e.g., light emitter and detector) that detects the change in intensity of light passing through the waste passageway 24.

An upstream passageway/tube 32, which is strategically positioned upstream of the sample well 16, has a first end (upstream end) connected to an air pump 34 and a second end (downstream end) coupled to the sample well 16 through a through lumen 13 in the hinged lid 14 such that the upstream passageway is in fluid communication with a top portion of the well where there is no liquid sample. Preferably, the air pump 34 has a variable or multi speed capability to allow for a low speed operation for loading the liquid sample into the analytical instrument 20 and a high speed operation for drying the lumens in the liquid path which include the sample passageway 18, transfer tube 22, lumen (not shown) inside the analytical instrument 20 between the input port 25 and exit port 26, and waste tube 24.

A flow control valve 36 controls the flow of air from the air pump 34 to the sample well 16. A vent passageway/tube 38 is coupled to the upstream passageway 32 between the flow control valve 36 and the sample holder 12. A relief valve 40 is positioned on the vent passageway 38 to relieve any excess air pressure beyond atmospheric pressure in the upstream passageway 32 into atmosphere. Preferably, the valves 36,40 are electronically controlled solenoid valves. A controller 42 is connected to and controls the operation of the air pump 34, flow control valve 36, relief valve 40, and sample sensor 30.

A method of loading and unloading the sample into and from the analytical instrument 20 will now be described. Initially the air pump 34 is off and both valves 36,40 are closed. An operator then raises the hinged lid 14 and pours the liquid sample into the sample well 16. The operator closes the hinged lid 14 fluidly sealing the sample well. The operator then signals the controller 42 to start the loading operation. Although not shown, the operator could press a button coupled to the controller 42 which signals the controller to start the loading operation. Alternatively, and also not shown, a switch could be built into the sample holder 12 which detects when the lid 14 is closed. In that case, the controller 42 can be programmed/configured to keep the pump 34 turned off regardless of the operator's wish until it receives an indication from the switch that the lid 14 is closed.

The controller 42 opens the flow control valve 36 and then starts the air pump 34. The air pressure of the upstream passageway 32 from the pump 34 forces the liquid sample downward in the well 16, up through the inclined passageway 18, through the transfer passageway 22 into the analytical instrument 20, then into the waste passageway 24.

The presence of the liquid sample is detected by the sample sensor 30 which then transmits a signal to the controller 42 indicating that the sample is present in the waste passageway 24. The controller 42 then performs a sequence of steps to stop the loading process. The controller turns off the air pump 34 and then closes the flow control valve 36. The controller 42 then turns on the relief valve 40 momentarily to release any residual pressure in the upstream passageway 32 which would otherwise continue to advance the liquid sample. Preferably, the relief valve 40 turns on for at least 0.1 second and at most 2 seconds. Most preferably, the controller 42 turns on the relief valve 40 for at least 0.25 second and at most 1 second.

Advantageously, once the lid 14 is closed, the entire operation of the above described loading process can be automatically controlled by the controller 42.

After the analysis of the liquid sample by the analytical instrument 20 is complete, the liquid sample will need to be unloaded. The unloading operation includes flushing of the liquid sample from the passageways, and cleaning and drying of the passageways. To do so, the operator signals the controller 42 to start the unloading operation. Although not shown, the operator could press a button coupled to the controller 42 which signals the controller to start the unloading operation.

In response, the controller 42 opens the flow control valve 1 and then turns on the air pump 34 which forces the liquid sample into the waste container 28. Preferably, the air pump 34 operates at a higher speed than during the loading steps since there is no need to be concerned about forming air bubbles and the higher speed allows the passageways and the sample well to be dried faster.

Once the liquid sample stops flowing into the waste container 28, cleaning and drying steps are performed. With the air pump 34 continuing to run, the operator raises the hinged lid 14, pours a cleaning solvent into the sample well 16, and closes the lid to clean the well and the passageways 18,22,24. These cleaning steps are repeated as needed to remove all residual liquid sample. After the last rinse is loaded, the controller 42 keeps the air pump 34 on for a few minutes to dry the entire liquid sample path.

Advantageously, once the unloading process is started, the entire operation of the above described unloading and cleaning process can be automatically controlled by the controller 42. Thus, after the controller 42 turns on the air pump 34 at the higher speed to blow out the remaining sample into the waste container 28, the pump continues to run while the operator opens and closes/locks the lid 14 to pour cleaning agent as many times as are needed to clear the sample passageways. The controller 42 is programmed to continue to run the air pump 34 for a predetermined time period, e.g., 5 minutes, to dry the sample well and the sample passageways, and then turn the pump off.

The conical shape of the sample well 16 and the inclined passageway 18 extending at an inclined upward angle from the bottom of the well provide many performance benefits. As the operator pours the liquid sample into the well 16, both the well and the inclined sample passageway 18 fill from the bottom under the action of gravity, which displaces air upwards. The upward displacement of air tends to eliminate the formation of slugs of liquid sample separated by trapped air. As a result, the liquid sample travels as a single body. This synergistically allows the sample sensor 30 to be a reliable indicator that the analytical instrument 20 is loaded fully without trapped air.

Figure 1:
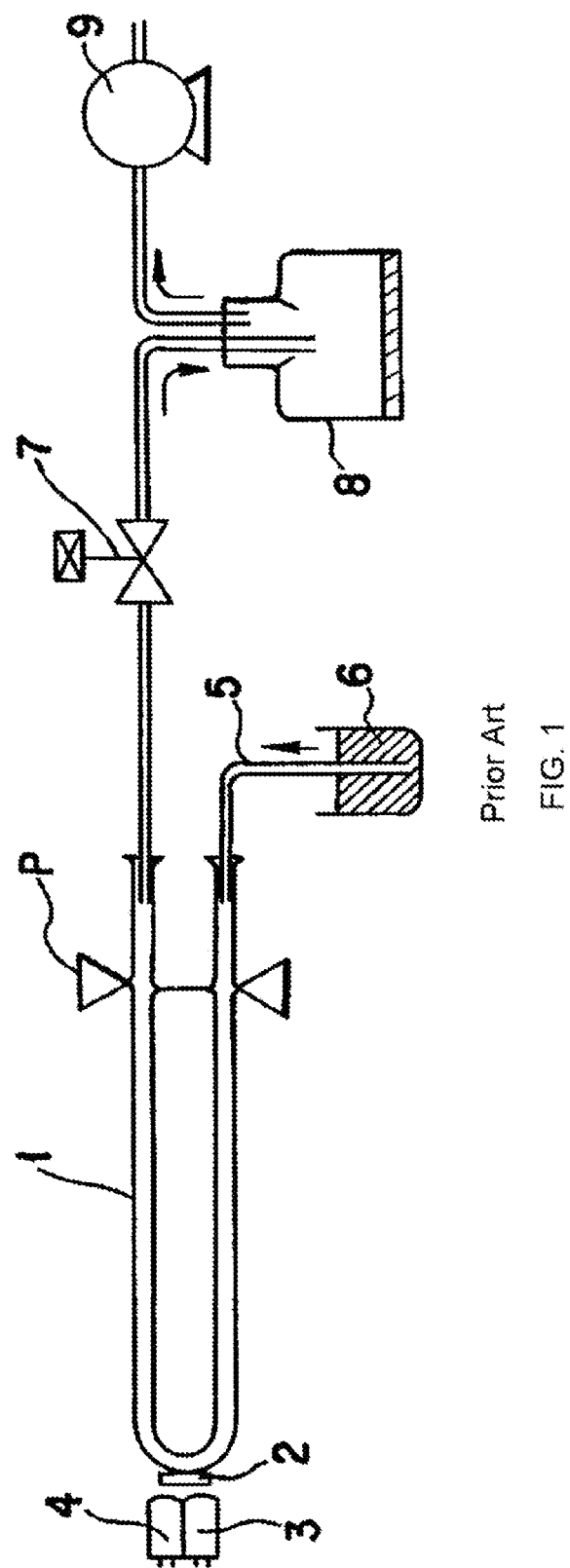
FIG. 1 is a sample loader for an analytical instrument according to the prior art.

Another important advantage of the form of the sample well 16 is that the entire liquid sample is forced out of the sample well. No liquid sample is left in the well 16 other than a film on the walls. The ability to load essentially the entire liquid sample together with the ability to use a sample sensor 30 reliably results in a system 10 that requires a minimum volume of sample per analysis. Another important advantage of the form of the sample well 16 is that the dip tube such as the one 5 shown in FIG. 1 has essentially moved inside of the wall of the well 16 and as a result, has no outside surface that would require cleaning.

Another important advantage is that the lid 14 sealing the sample well 16, together with the closed valves 36,40, prevents the liquid sample from syphoning out of the analytical instrument 20 during analysis. It is the sealed lid 14 that allows the valves to be placed in the air path rather than in the liquid sample path.

As a result, the present invention provides an efficient and relatively inexpensive device for loading a liquid sample into an analytical instrument without using syringes, without using disposable consumables and with using only a minimal volume of the sample liquid. Because the loading operation uses a pressure mode of the air pump to push the liquid sample rather than pull by vacuum, the present invention is also suitable for the widest variety of sample types including those with high viscosity.

Figure 3:
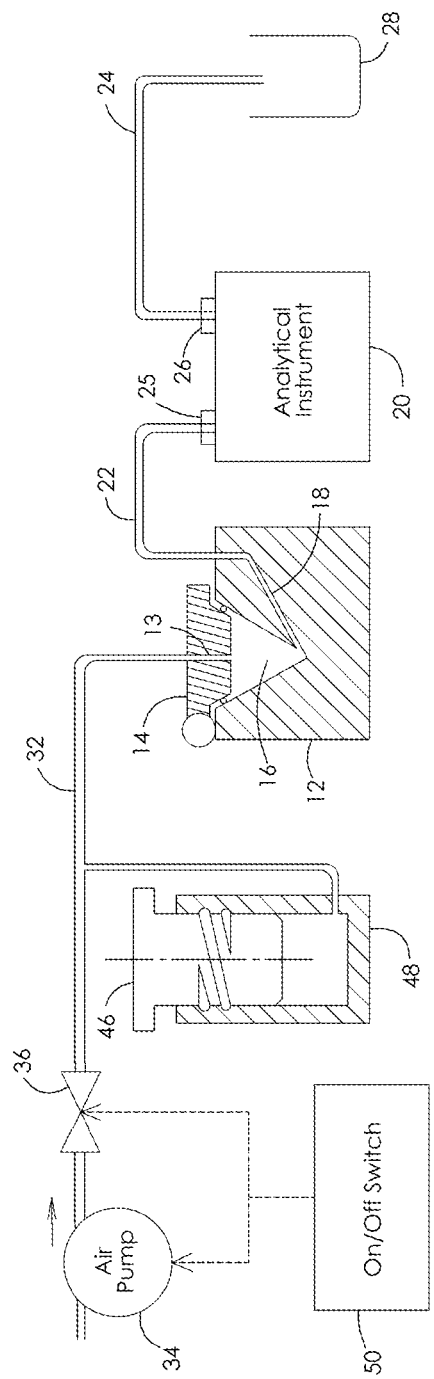
FIG. 3 illustrates a sample loader for an analytical instrument according to an alternative embodiment of the present invention.

FIG. 3 is an alternative sample loader for an analytical instrument. While the loader is similar to that of FIG. 2, there are some differences. In this embodiment, a controller is replaced with a simple on/off switch 50 which connects to and controls the pump 34. A second pump comprising a threaded piston 46 and a cylinder 48 is coupled to the upstream passageway 32. Unlike FIG. 2, the sample loader in FIG. 3 does not have a sample sensor 30.

In operation, the pump 34 is turned off by the switch 50, valve 36 is closed and the threaded piston 46 is in a raised position. To load the sample, the user places the liquid sample into the well 16 and closes the lid 14 to seal the well 16. The user then rotates the threaded piston 46 inward in cylinder 48 which creates pressure to achieve the desired fill of the liquid sample into the analytical instrument 20.

Once measurements are made by the analytical instrument 20, a cleaning operation needs to be performed. The user actuates the switch 50 to open the flow control valve 36 and turn on the pump 34 to blow out the liquid sample in the well 16 and all the passageways downstream of the well. Cleaning solvents are then loaded in the well 16 and pushed through with the air pump 34 in a similar manner as the liquid sample.

The advantages of this arrangement are simplicity and lower cost as the sample sensor 30 is eliminated and controller 42 is replaced with a simple switch. Moreover, very fine control of the sample loading can be achieved through the rotation of the threaded piston 46.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A liquid sample loader for an analytical instrument comprising:
    a sample holder having a sample well for holding a liquid sample and a sample passageway having a first end connected to a bottom portion of the sample well and extending upwardly at an inclined angle directly from the first end;
    an upstream passageway coupled to an upper portion of and in fluid communication with the sample well;
    a transfer passageway coupled between the sample passageway and the analytical instrument for carrying the sample into the analytical instrument; and
    a pump coupled to the upstream passageway and positioned upstream from the sample holder.

2. The liquid sample loader of claim 1, further comprising a controller that controls the pump to push the sample in the sample well through the sample passageway toward the measuring instrument.

3. The liquid sample loader of claim 1, further comprising a sensor positioned near an output port of the analytical instrument and adapted to transmit a presence signal indicative of the presence of the sample to the controller, wherein the controller stops the pump when the presence signal is received.

4. The liquid sample loader of claim 1, wherein the sample holder includes a lid adapted to receive the upstream passageway such that the upstream passageway is in fluid communication with the sample well when the lid is closed.

5. The liquid sample loader of claim 1, wherein the sample holder includes a hinged lid adapted to fluidly seal the sample well and to receive the upstream passageway such that the upstream passageway is in fluid communication with the sample well when the lid is closed.

6. The liquid sample loader of claim 1, further comprising a flow control valve coupled between the pump and the sample holder to control the loading of the sample into the analytical instrument, wherein the controller is adapted to turn off the flow control valve when the sample has been loaded.

7. The liquid sample loader of claim 6, further comprising a relief valve positioned between the flow control valve and the sample holder, the relief valve having a first end coupled to the upstream passageway and a second end coupled to atmosphere, such that when the sample has been loaded into the analytical instrument, the controller is adapted to turn off the pump, close the flow control valve and then open the relief valve momentarily to release residual air pressure in the upstream passageway into the atmosphere.

8. The liquid sample loader of claim 1, further comprising:
a sample sensor positioned near an output port of the analytical instrument and adapted to generate a presence signal indicative of the presence of the liquid sample;
a flow control valve coupled between the pump and the sample holder to control the loading of the sample into the analytical instrument;
a relief valve positioned between the flow control valve and the sample holder, the relief valve having a first end coupled to the upstream passageway and a second end coupled to atmosphere, such that when the controller receives the presence signal from the sample sensor, the controller is adapted to turn off the pump, close the flow control valve and open the relief valve momentarily to release residual air pressure in the upstream passageway into the atmosphere;
wherein the sample holder includes a hinged lid adapted to fluidly seal the sample well when closed and to receive the upstream passageway such that the upstream passageway is in fluid communication with the sample well when the lid is closed.

9. The liquid sample loader of claim 8, wherein the controller is adapted to open the relief valve momentarily for 1 second or less.

10. A liquid sample loader for an analytical instrument comprising:
a sample holder having a sample well for holding a liquid sample and a sample passageway in fluid communication with the well and extending upwardly at an inclined angle directly from a bottom of the sample well;
an air pump positioned upstream from the sample holder;
an upstream passageway coupled between the sample holder and the air pump;
a flow control valve disposed on the upstream passageway between the air pump and the sample holder;
a controller that controls the flow control valve and the air pump to push air through the upstream passageway in a downstream direction so as to push the sample in the sample well through the sample passageway toward the analytical instrument.

11. The liquid sample loader of claim 10, further comprising a sample sensor positioned near a sample output port of the analytical instrument and adapted to transmit a presence signal indicative of the presence of the sample to the controller, wherein the controller stops the pump and the flow control valve when the presence signal is received.

12. The liquid sample loader of claim 10, wherein the sample holder includes a lid adapted to receive the upstream passageway such that the upstream passageway is in fluid communication with the sample well when the lid is closed.

13. The liquid sample loader of claim 10, further comprising a relief valve positioned between the flow control valve and the sample holder, the relief valve having a first end coupled to the upstream passageway and a second end coupled to atmosphere, such that when the sample has been loaded into the analytical instrument, the controller is adapted to turn off the pump, close the flow control valve and open the relief valve momentarily for 1 second or less to release residual air pressure in the upstream passageway into the atmosphere.

* * * * *